(12) United States Patent
Makioka

(10) Patent No.: US 10,989,697 B2
(45) Date of Patent: Apr. 27, 2021

(54) BREATH ANALYZER

(71) Applicant: SHIMADZU CORPORATION, Kyoto (JP)

(72) Inventor: Shingo Makioka, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 179 days.

(21) Appl. No.: 15/923,037

(22) Filed: Mar. 16, 2018

(65) Prior Publication Data
US 2019/0285593 A1  Sep. 19, 2019

(51) Int. Cl.
| | |
|---|---|
| *G01N 30/30* | (2006.01) |
| *G01N 30/14* | (2006.01) |
| *G01N 30/08* | (2006.01) |
| *G01N 33/497* | (2006.01) |

(52) U.S. Cl.
CPC ............ *G01N 30/30* (2013.01); *G01N 30/08* (2013.01); *G01N 30/14* (2013.01); *G01N 33/497* (2013.01)

(58) Field of Classification Search
CPC ...... G01N 30/30; G01N 33/497; G01N 30/08; G01N 30/14; G01N 2030/121; G01N 2030/128; G01N 30/7206
See application file for complete search history.

(56) References Cited

U.S. PATENT DOCUMENTS

| | | | |
|---|---|---|---|
| 6,190,613 B1 | 2/2001 | Watanabe et al. | |
| 6,341,520 B1* | 1/2002 | Satoh ................. | G01N 30/88 422/84 |
| 2003/0015019 A1 | 1/2003 | O'Brien | |
| 2011/0100093 A1* | 5/2011 | Kawana ............. | G01N 30/8658 73/23.42 |

FOREIGN PATENT DOCUMENTS

| | | |
|---|---|---|
| JP | 2000-171449 A | 6/2000 |
| JP | 2003-521688 A | 7/2003 |
| JP | 3135149 U | 9/2007 |
| JP | 2017-058284 A | 3/2017 |

OTHER PUBLICATIONS

Communication dated Aug. 28, 2018 from the Japanese Patent Office in counterpart Application No. 2015-184283.

* cited by examiner

*Primary Examiner* — David Z Huang
(74) *Attorney, Agent, or Firm* — Sughrue Mion, PLLC

(57) ABSTRACT

A cooling unit (cryo-focus unit) cools breath introduced into a carrier gas from a sample introduction unit, to trap volatile components in the breath into a column. A heater heats the volatile components trapped in the column to desorb the volatile components. A mass spectrometry (MS) section detects the volatile components desorbed by the heater and separated in a process of passing through the column. The breath introduced into the carrier gas from the sample introduction unit is cooled by the cooling unit, whereby more volatile components in the breath are trapped, and those volatile components can be desorbed, and can be detected by the MS section.

10 Claims, 2 Drawing Sheets

BREATH ANALYZER

BACKGROUND OF THE INVENTION

Field of the Invention

The present invention relates to a breath analyzer for analyzing volatile components in breath.

Description of the Related Art

Conventionally, a technique (a breath analysis technique) for diagnosing diseases by analyzing volatile components in breath has been known. For example, such a breath analysis technique includes a configuration in which, by using a gas chromatograph (GC) or a gas chromatograph mass spectrometer (GC/MS), breath is introduced into a column together with a carrier gas, and volatile components in breath, which are separated in a course of passing through the column, are detected by a detection unit (see, for example, JP-U-3135149).

However, in a configuration in which breath is merely introduced into the column, the volatile components in breath cannot be sufficiently separated, and high detection sensitivity may not be obtained in some cases. Therefore, as such a breath analysis technique, for example, a solid phase adsorption method is generally used, in which the volatile components in breath are adsorbed to an adsorbent such as a polymer, and the volatile components are analyzed by thermal desorption.

However, when the solid phase adsorption method is used, the volatile components in breath, which can be adsorbed, are limited depending on the adsorbent to be used. Therefore, there is a problem that it is difficult to simultaneously detect more volatile components in breath. In particular, in the case of searching for a specific component by which it is possible to diagnose a disease from a minute amount of the volatile components in breath, it is important that more volatile components can be detected by one analysis. Therefore, there is a possibility that a sufficient analysis result cannot be obtained by the solid phase adsorption method.

SUMMARY OF THE INVENTION

The present invention has been made in view of the above circumstances. It is an object of the present invention to provide a breath analyzer capable of detecting more volatile components in breath.

(1) A breath analyzer according to the present invention includes: a column; a carrier gas supply unit; a sample introduction unit; a cooling unit; a heating unit; and a detection unit. The carrier gas supply unit supplies a carrier gas into the column. The sample introduction unit introduces breath into the carrier gas supplied from the carrier gas supply unit into the column. The cooling unit cools the breath introduced from the sample introduction unit into the carrier gas, to trap a volatile component in the breath into the column. The heating unit heats the volatile components trapped in the column to desorb the volatile components. The detection unit detects the volatile component desorbed by the heating unit and separated in a process of passing through the column.

With such a configuration, the breath introduced from the sample introduction unit into the carrier gas is cooled by the cooling unit, whereby more volatile components in the breath can be trapped in the column. Then, the volatile components trapped in the column are heated by the heating unit, whereby the volatile components can be desorbed sequentially from low boiling volatile components, and the desorbed volatile components can be separated in the column and sequentially detected by the detection unit. Therefore, more volatile components in the breath can be detected.

The breath analyzer described above is not limited to such a configuration including the cooling unit and the heating unit individually, and may have a configuration in which the cooling unit and the heating unit are configured by a temperature control unit having both of a cooling function and a heating function.

With such a configuration, the volatile components in the breath are cooled by the cooling function and trapped in the column, and thereafter, an operation of the cooling function is stopped and an operation of the heating function is started, whereby the trapped volatile components are heated as they are. In this way, after the introduction of the breath by the sample introduction unit, the volatile components in the breath, which are trapped in the column, can be smoothly heated and desorbed.

(2) The breath analyzer may further include a column oven that houses the column. In this case, the cooling unit and the heating unit may be provided in the column oven.

With such a configuration, if the operation of the cooling unit provided in the column oven is stopped after the volatile components in the breath are cooled by the cooling unit and are trapped in the column, the trapped volatile components are heated as they are by the heating unit also provided in the column oven. In this way, after the introduction of the breath by the sample introduction unit, the volatile components in the breath, which are trapped in the column, can be smoothly heated and desorbed.

(3) The breath analyzer may further include a control unit that stops an operation of the cooling unit while the carrier gas is kept on being supplied into the column by the carrier gas supply unit after the breath is introduced by the sample introduction unit.

With such a configuration, when the operation of the cooling unit is stopped after the introduction of the breath by the sample introduction unit, the volatile components desorbed in an ascending order of the boiling point pass through the column by the continuously supplied carrier gas. As a result, the desorbed volatile components smoothly pass through the column, and the volatile components separated in the column are satisfactorily detected by the detection unit.

(4) The control unit may stop the operation of the cooling unit after a lapse of a predetermined time after the breath is introduced by the sample introduction unit.

With such a configuration, oxygen, nitrogen and the like, which are contained in the breath, pass through the column for the predetermined time after the introduction of the breath by the sample introduction unit, and thereafter, the operation of the cooling unit is stopped. In this way, oxygen, nitrogen and the like, which are contained in the breath, can be prevented from adversely affecting a detection result, so that a better detection result can be obtained.

According to the present invention, the breath introduced into the carrier gas from the sample introduction unit is cooled by the cooling unit, whereby more volatile components in the breath can be trapped, and those volatile components can be desorbed, and can be detected by the detection unit.

DETAILED DESCRIPTION OF THE PREFERRED EMBODIMENTS

1. Configuration of Breath Analyzer

Figure 1:
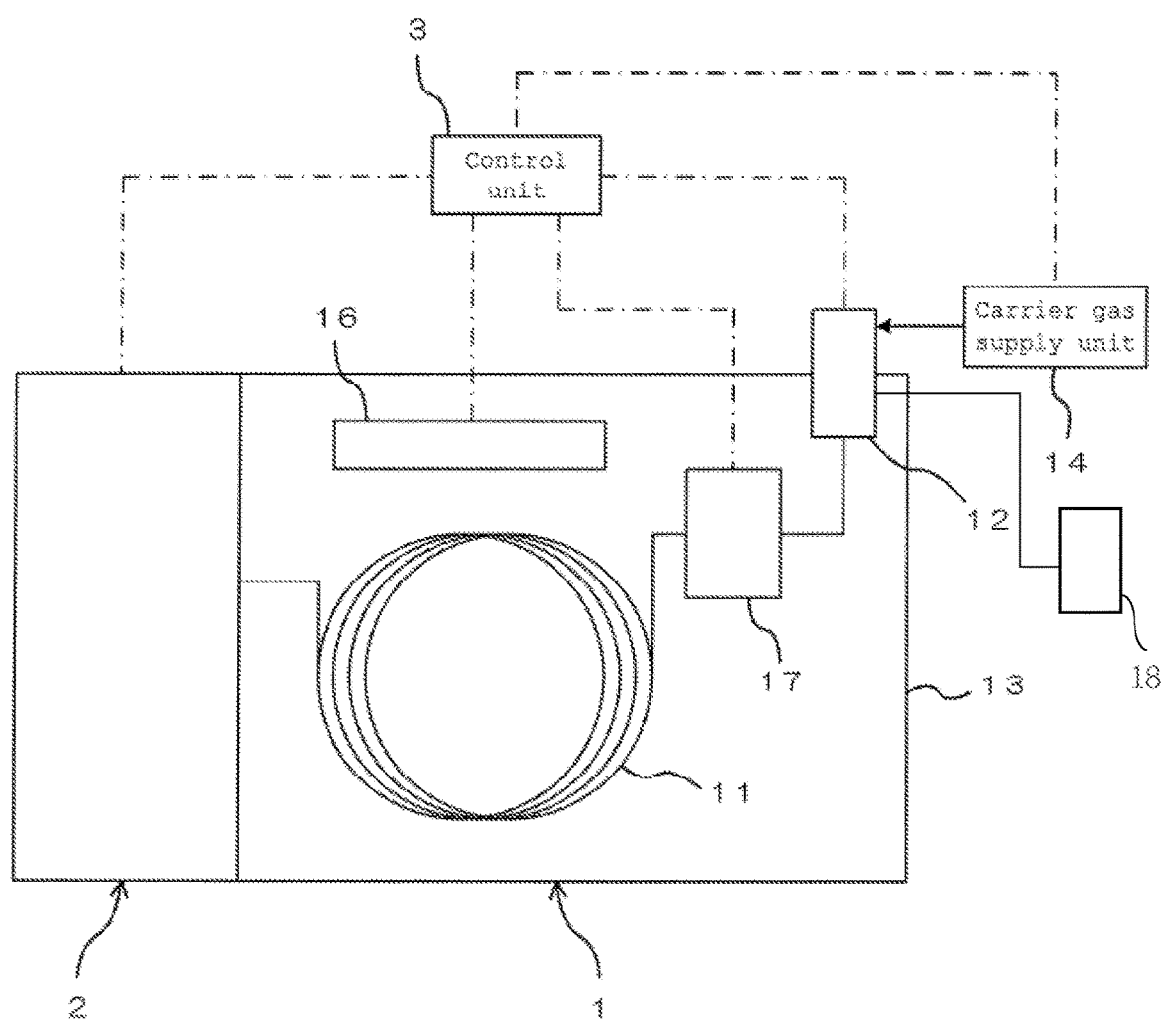
FIG. 1 is a schematic diagram showing a configuration example of a breath analyzer according to an embodiment of the present invention.

FIG. 1 is a schematic diagram showing a configuration example of a breath analyzer according to an embodiment of the present invention. This breath analyzer is configured by a gas chromatograph mass spectrometer (GC/MS) including a gas chromatograph section (GC section 1) and a mass spectrometry section (MS section 2).

For example, the GC section 1 includes a column 11, a sample introduction unit 12, a column oven 13, a carrier gas supply unit 14, a heater 16 and a cooling unit 17. The column 11 is, for example, a capillary column, in which an upstream end is connected to the sample introduction unit 12, and a downstream end is connected to the MS section 2.

The column 11 is housed in the column oven 13 together with the heater 16, the cooling unit 17 and the like. The column oven 13 is for heating the column 11. At the time of analysis, the heater 16 is driven, so that the analysis is performed while heating the column 11.

In the sample introduction unit 12, a sample vaporizing chamber (not shown) is formed. Breath to be analyzed is introduced into the sample vaporizing chamber of the sample introduction unit 12. In addition, a carrier gas is supplied from the carrier gas supply unit 14 to the sample vaporizing chamber. As the carrier gas, for example, an inert gas such as He gas is used. In the sample vaporizing chamber, the breath is introduced into the carrier gas supplied from the carrier gas supply unit 14, and the carrier gas mixed with the breath is introduced into the column 11 from the sample vaporizing chamber.

In FIG. 1, a split flow path 18 for discharging part of the gas in the sample vaporizing chamber to the outside at a predetermined split ratio is connected to the sample introduction unit 12. When introducing the carrier gas together with the sample into the column 11, part of the carrier gas is discharged from the split flow path 18 to the outside, whereby the sample can be introduced into the column 11 using a split introduction method. For example, in the case of injecting a sample with a low concentration in the order of ppb, a splitless introduction method is sometimes used, in which an entire amount of the sample is introduced into the column 11 by closing the split flow path 18 using a valve (not shown). In the case of analyzing the breath as a sample, it is necessary to introduce the entire amount of the sample into the column 11 (the latter case: the splitless introduction method) since a concentration of volatile components in the breath is low. In the present embodiment, breath of, for example, 10 ml or more is injected into the sample vaporizing chamber using a syringe 9 or the like in the sample introduction unit 12 (since the cooling unit 17 is used), and the entire amount of the breath is introduced into the column 11.

The breath introduced into the carrier gas is cooled by the cooling unit 17 immediately after being supplied into the column 11. The cooling unit 17 is provided in the vicinity of an upstream end of the column 11. Specifically, the cooling unit 17 is provided at a position within 50 cm, more preferably within 30 cm from the upstream end to a downstream end side in the column 11.

The cooling unit 17 cools the column 11 from the outside. A gas cooled by a coolant such as liquid nitrogen is supplied to the cooling unit 17, and the column 11 is cooled by heat exchange between the gas and the column 11. A temperature of a portion of the column 11, which is cooled by the cooling unit 17, is, for example, −160 to −190° C., but the temperature is not limited to this. The temperature varies depending on a type of the coolant, and is preferably, for example, −60° C. or less, more preferably −100° C. or less.

In this manner, the cooling unit 17 functions as a cryo-focus unit that cools the column 11 to trap the volatile components in the breath inside the cooled portion of the column 11. That is, a part or all of the volatile components in the breath are collected in the vicinity of the upstream end of the column 11, and are held without flowing to the downstream side of the upstream end. Meanwhile, oxygen, nitrogen and the like in the breath are not trapped even if cooled by the cooling unit 17, and will flow to the downstream side in the column 11.

When an operation of the cooling unit 17 is stopped, the column 11, which includes the portion cooled by the cooling unit 17, is heated by the heater 16. That is, the column 11 is provided in the column oven 13 together with the heater 16 and the cooling unit 17, and accordingly, while the cooling unit 17 is operating, the vicinity of the upstream end of the column 11 is cooled even if the heater 16 is operating. However, when the operation of the cooling unit 17 is stopped, the vicinity of the upstream end of the column 11 is heated by the operating heater 16.

As a result, the temperature in the vicinity of the upstream end of the column 11 gradually increases, and approaches a temperature in the column oven 13. At this time, the volatile components in the breath trapped in the vicinity of the upstream end of the column 11 volatilize in order from a lowest boiling volatile component. As a result, the volatile components are desorbed from a state of being trapped in the column 11, and flow to the downstream side of the column 11. That is, the heater 16 constitutes a heating unit that heats the volatile components trapped in the column 11 to desorb the volatile components. As such low boiling volatile components, hydrogen sulfide ($H_2S$), formaldehyde ($CH_2O$) and the like can be exemplified, but the low boiling volatile components are not limited thereto.

The volatile components in the breath, which are desorbed by the heating of the heater 16, are separated in the process of passing through the column 11, and are sequentially guided to the MS section 2 as a detection unit. The MS section 2 performs mass spectrometry on the volatile components sequentially guided from the column 11. A method of the mass spectrometry by the MS section 2 is not particularly limited, but for example, a method using a quadrupole mass spectrometer can be adopted.

In this case, the volatile components sequentially guided from the column 11 are ionized in an ionization unit (not shown), and ions thus obtained are sent to the quadrupole mass spectrometer. In the quadrupole mass spectrometer, only ions having a specific m/z (mass-to-charge ratio) selectively pass between four electrodes, and ions that have passed therethrough are detected by a detector. As a result, a relationship between m/z and detection intensity at the detector is measured as a mass spectrum, and mass spectrometry is achieved.

Operations of the sample introduction unit 12, the carrier gas supply unit 14, the heater 16, the cooling unit 17 and the MS section 2 are controlled by a control unit 3 including a CPU (Central Processing Unit), for example. The control unit 3 may be provided in either the GC section 1 or the MS section 2, or may be configured by a control unit provided separately from the GC section 1 and the MS section 2.

2. Operations During Breath Analysis

Figure 2:
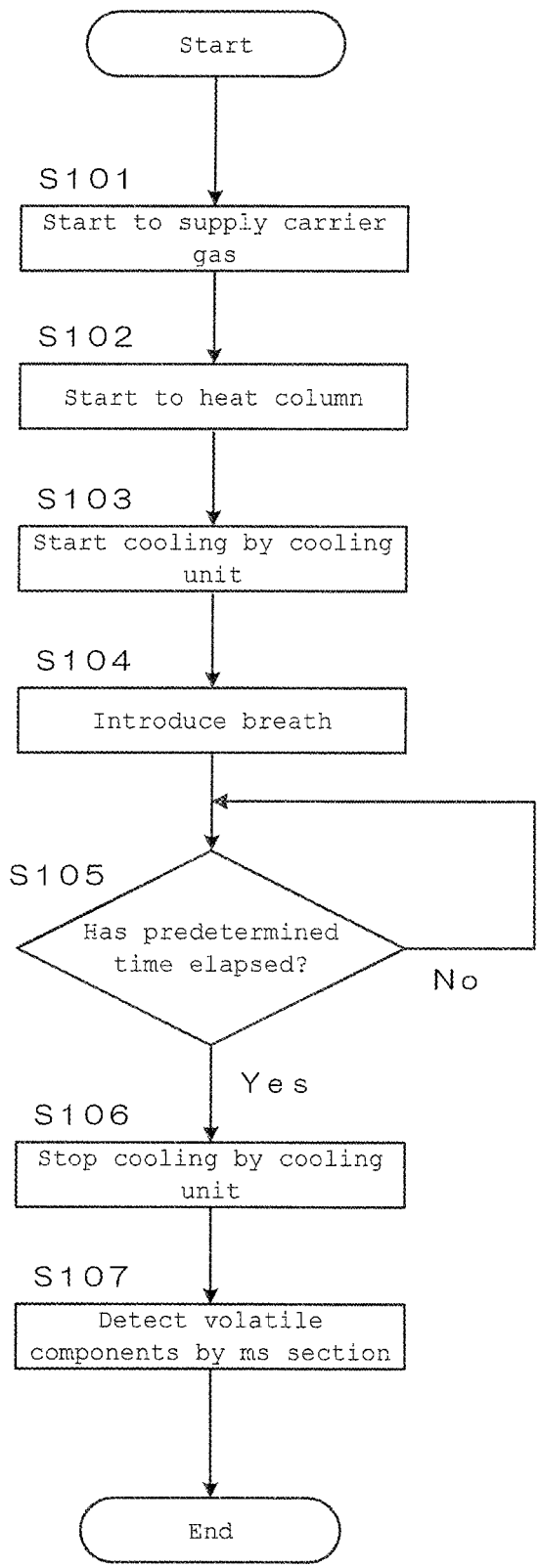
FIG. 2 is a flowchart showing a flow of processing by a control unit during breath analysis.

FIG. 2 is a flowchart showing a flow of the processing by the control unit 3 during breath analysis.

When the volatile components in the breath are analyzed, the supply of the carrier gas from the carrier gas supply unit 14 is started (Step S101), and the heating of the column 11 by the heater 16 is started (Step S102). During analysis that follows, the carrier gas is continuously supplied and the column 11 is continuously heated.

Then, first, the cooling by the cooling unit 17 is started (Step S103), whereby the vicinity of the upstream end of the column 11 is cooled. When the vicinity of the upstream end of the column 11 is sufficiently cooled and the temperature of the vicinity of the upstream end is stabilized, the breath is introduced from the sample introduction unit 12 to the carrier gas supplied into the column 11 (Step S104).

Thereafter, the cooling unit 17 is kept operating until a predetermined time elapses, and when the predetermined time has elapsed (Yes in Step S105), the cooling by the cooling unit 17 is stopped (Step S106). That is, after the introduction of the breath by the sample introduction unit 12, the operation of the cooling unit 17 is stopped after a lapse of the predetermined time while the carrier gas is kept on being supplied into the column 11 by the carrier gas supply unit 14.

Although not particularly limited, the predetermined time described above is preferably 180 to 500 seconds, more preferably 450 to 500 seconds. The predetermined time is obtained based on, for example, a length of the column 11, a flow velocity of the carrier gas or the like, and is set to a value sufficient to allow the breath (oxygen, nitrogen and the like) after the volatile components are trapped in the column 11 to pass through the column 11.

When the cooling by the cooling unit 17 is stopped (Step S106), the temperature in the vicinity of the upstream end of the column 11 is gradually increased by the heating of the heater 16, and the volatile components in the breath, which are trapped in the column 11, are desorbed in order from the low boiling volatile component, and flow to the downstream side of the column 11. Then, the volatile components separated in the process of passing through the column 11 are sequentially detected by the MS section 2 (Step S107), whereby the mass spectrometry is performed.

3. Operation and Effect (1) In the present embodiment, as shown in FIG. 1, the breath introduced into the carrier gas from the sample introduction unit 12 is cooled by the cooling unit 17, whereby more volatile components in the breath can be trapped in the column 11. Then, the volatile components trapped in the column 11 are heated by the heater 16, whereby the volatile components can be desorbed sequentially from the low boiling volatile components, and the desorbed volatile components can be separated in the column 11 and sequentially detected by the MS section 2. Therefore, more volatile components in the breath can be detected.

(2) In particular, in the present embodiment, as shown in FIG. 1, the cooling unit 17 and the heater 16 are provided in the column oven 13 together with the column 11. Therefore, if the operation of the cooling unit 17 provided in the column oven 13 is stopped after the volatile components in the breath are cooled by the cooling unit 17 and are trapped in the column 11, the trapped volatile components are heated as they are by the heater 16 also provided in the column oven 13. In this way, after the introduction of the breath by the sample introduction unit 12, the volatile components in the breath, which are trapped in the column 11, can be smoothly heated and desorbed.

(3) Moreover, in the present embodiment, as shown in FIG. 2, after the breath is introduced by the sample introduction unit 12 (Step S104), the operation of the cooling unit 17 is stopped while the carrier gas is kept on being supplied into the column 11 (Step S106). Therefore, when the operation of the cooling unit 17 is stopped after the introduction of the breath by the sample introduction unit 12, the volatile components desorbed in an ascending order of the boiling point pass through the column 11 by the continuously supplied carrier gas. As a result, the desorbed volatile components smoothly pass through the column 11, and the volatile components separated in the column 11 are satisfactorily detected by the MS section 2.

(4) In particular, in the present embodiment, as shown in FIG. 2, after the breath is introduced by the sample introduction unit 12 (Step S104) and after the predetermined time has elapsed (Yes in Step S105), the operation of the cooling unit 17 is stopped (Step S106). That is, oxygen, nitrogen and the like, which are contained in the breath, pass through the column 11 for the predetermined time after the introduction of the breath by the sample introduction unit 12, and thereafter, the operation of the cooling unit 17 is stopped. In this way, oxygen, nitrogen and the like, which are contained in the breath, can be prevented from adversely affecting a detection result, so that a better detection result can be obtained.

4. Modified Example

In the above embodiment, the description has been given of the case where the breath analyzer is configured by the gas chromatograph mass spectrometer in which the MS section 2 detects the volatile components separated in the process of passing through the column 11. However, the present invention is not limited to such a configuration. For example, such a configuration may be adopted, in which the volatile components separated in the process of passing through the column 11 are detected by another detector such as a flame ionization detector (FID). In this case, the breath analyzer is not limited to the gas chromatograph mass spectrometer including the GC section 1 and the MS section 2, but may be configured by a gas chromatograph including only the GC section 1.

Furthermore, in the above embodiment, the description has been given of the configuration in which the operations of the breath analyzer for analyzing the volatile components in the breath are automatically performed by the processing of the control unit 3 as exemplified in FIG. 2. However, the present invention is not limited to such a configuration, and may adopt a configuration in which at least a part of the processing as exemplified in FIG. 2 is manually performed by an operator.

The heater 16 and the cooling unit 17 are not limited to the respective structures provided separately, and for example, a heating unit and a cooling unit may be configured by a temperature control unit having both a cooling function and a heating function. In this case, the volatile components in the breath are cooled by the cooling function and trapped in the column 11, and thereafter, an operation of the cooling function is stopped and an operation of the heating function is started, whereby the trapped volatile components are heated as they are. In this way, after the introduction of the breath by the sample introduction unit 12, the volatile components in the breath, which are trapped in the column 11, can be smoothly heated and desorbed.

What is claimed is:

1. A breath analyzer comprising:
    a column;
    a carrier gas supply unit that supplies a carrier gas into the column;
    a sample introduction unit that introduces breath into the carrier gas supplied from the carrier gas supply unit into the column;
    a cooling unit that cools the breath introduced from the sample introduction unit into the carrier gas, to trap a volatile component in the breath into the column;
    a heating unit that heats the volatile component trapped in the column to desorb the volatile component;
    a detection unit that detects the volatile component desorbed by the heating unit and separated in a process of passing through the column; and
    a control unit that keeps the carrier gas being supplied into the column by the carrier gas supply unit after the breath is introduced by the sample introduction unit.

2. The breath analyzer according to claim 1, further comprising a column oven that houses the column,
    wherein the cooling unit and the heating unit are provided in the column oven.

3. The breath analyzer according to claim 1, wherein the control unit stops an operation of the cooling unit while the carrier gas is kept on being supplied into the column by the carrier gas supply unit after the breath is introduced by the sample introduction unit.

4. The breath analyzer according to claim 3, wherein the control unit stops the operation of the cooling unit after a lapse of a predetermined time after the breath is introduced by the sample introduction unit.

5. The breath analyzer according to claim 4, wherein the predetermined time is a predetermined time for oxygen and nitrogen contained in the breath to pass through the column.

6. The breath analyzer according to claim 1, further comprising a split flow path for discharging part of the carrier gas in a sample vaporizing chamber to the outside of the breath analyzer at a predetermined ratio.

7. The breath analyzer according to claim 6, wherein the split flow path is connected to the sample introduction unit.

8. The breath analyzer according to claim 6, wherein the sample vaporizing chamber is in the sample introduction unit.

9. The breath analyzer according to claim 1, wherein the cooling unit is provided at a position within 50 cm from an upstream end to a downstream end side of the column.

10. The breath analyzer according to claim 9, wherein the cooling unit is provided at a position within 30 cm from the upstream end to the downstream end side of the column.

* * * * *